United States Patent
Tezuka et al.

(10) Patent No.: US 7,005,649 B1
(45) Date of Patent: Feb. 28, 2006

(54) MASK BLANKS INSPECTION METHOD AND MASK BLANK INSPECTION TOOL

(75) Inventors: Yoshihiro Tezuka, Tsukuba (JP); Masaaki Ito, Nerima (JP)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 10/971,786

(22) Filed: Oct. 21, 2004

(30) Foreign Application Priority Data

Sep. 13, 2004 (JP) .............................. 2004-265399

(51) Int. Cl.
*G01J 1/42* (2006.01)
(52) U.S. Cl. ..................................................... 250/372
(58) Field of Classification Search ................. 250/372
See application file for complete search history.

(56) References Cited

U.S. PATENT DOCUMENTS

| | | | |
|---|---|---|---|
| 5,754,678 A * | 5/1998 | Hawthorne et al. | 382/149 |
| 5,790,251 A * | 8/1998 | Hagiwara | 356/491 |
| 2005/0008944 A1 * | 1/2005 | Cerrina et al. | 430/5 |

FOREIGN PATENT DOCUMENTS

| | | |
|---|---|---|
| JP | 7072093 | 3/1995 |
| JP | 2002328099 | 11/2002 |
| JP | 2003114200 | 4/2003 |

\* cited by examiner

*Primary Examiner*—David Porta
*Assistant Examiner*—Marcus Taningco
(74) *Attorney, Agent, or Firm*—Blakely, Sokoloff, Taylor & Zafman LLP (57) ABSTRACT

Embodiments include determining whether defects exist in an extreme ultraviolet (EUV) light mask blank. Incident EUV light scattered or diffused by abnormalities in the layers of the mask blank may be measured, normalized, and compared to threshold values to determine if and where a defect exists. Normalizing may be performed by dividing a light intensity value for a pixel by the average of light intensity values for one or more rings of surrounding pixels. A defect may be determined by considering whether the normalized intensity value for a pixel is greater than a pixel threshold to identify the pixel is a candidate for a location with a defect; and by determining whether the sum of normalized light intensity values for a block of pixels including the pixel satisfies a pixel block threshold to determine whether the block scatters or diffuses a critical amount of light to identify a defect.

14 Claims, 5 Drawing Sheets

MASK BLANKS INSPECTION METHOD AND MASK BLANK INSPECTION TOOL

CROSS-REFERENCE TO RELATED APPLICATION

This application claims the benefit of the earlier filing date of co-pending Japanese Application No. 265399/2004, filed Sep. 13, 2004, by Intel Corporation, titled "Mask Blanks Inspection Method and Mask Blank Inspection Tool", and incorporated herein by reference.

BACKGROUND

1. Field

Circuit patterning and more particularly to masks used to pattern light sensitive material on substrates or wafers.

2. Background

Patterning is the series of operations that results in the removal of selected portions of surface layers added on a substrate, such as a wafer. Patterning creates the surface parts of devices that make-up a circuit. One goal of patterning is to create in or on the wafer surface, the parts of the device or circuit in the exact dimensions (feature size) required by the circuit design and to locate the parts in their proper location on the wafer surface.

Generally, patterning is accomplished through photolithography techniques. For example, photolithography may be a multi-operation pattern transfer process wherein a pattern contained on a reticle, photo mask, etch mask, or multi-layers mask is transferred onto the surface of a wafer or substrate through a lithographic imaging operation, and a light sensitive material (e.g., photoresist) is developed on the wafer. One goal of circuit designers is to reduce the feature size (the critical dimension) of devices of a circuit, i.e., reduce the smallest feature patternable. A reduction in wavelength of light used in patterning will reduce the critical dimension. Thus, the patterning wavelength can be reduced to under 200 nanometers, and can lie in the extreme ultraviolet (EUV) light region to reduce the critical dimension to 100 nanometers or less.

In the general course of patterning, the image of a reticle or photo mask is projected onto a wafer or substrate surface by an imaging system. EUV light radiation, however, does not pass through quartz or glass, and is therefore typically projected using reflective optics. For example, a reticle or photo mask for EUV light patterning of a light sensitive material may include a multi-layer mask that is created by forming light absorbing material on certain portions of a substrate covered with multiple layers of a reflective material (e.g., a patterning mask). The substrate having only multiple layers of reflective material may be referred to as a "mask blank" (e.g., such as a substrate having multiple layers of reflective material, prior to forming the light absorbing material).

It is important to be able to inspect an EUV light mask blank for defects that may cause errors in the imaging or patterning of the light sensitive material, such as by causing unwanted variations in the image of features (e.g., such as critical features) patterned on that material by the patterning mask formed from that mask blank. Specifically, because of the wavelength of EUV light used to expose the light sensitive material, a small bump with a height as low as two nanometers on the surface of a multi-layered mask blank may cause errors in the imaging or patterning of the light sensitive material, and thus be a defect in the mask blank. Therefore, EUV light patterning photo mask blanks may be inspected during manufacture, after manufacture, prior to shipment, or after shipment to detect "critical defects" (e.g., such as defects that may cause an error in patterning) while minimizing detection of "false defects" (e.g., such as defects that do not cause errors in patterning substantial enough to affect the critical dimension of features to be formed).

BRIEF DESCRIPTION OF THE DRAWINGS

Various features, aspects and advantages will become more thoroughly apparent from the following detailed description, the set of claims, and accompanying drawings in which:

DETAILED DESCRIPTION

Figure 1:
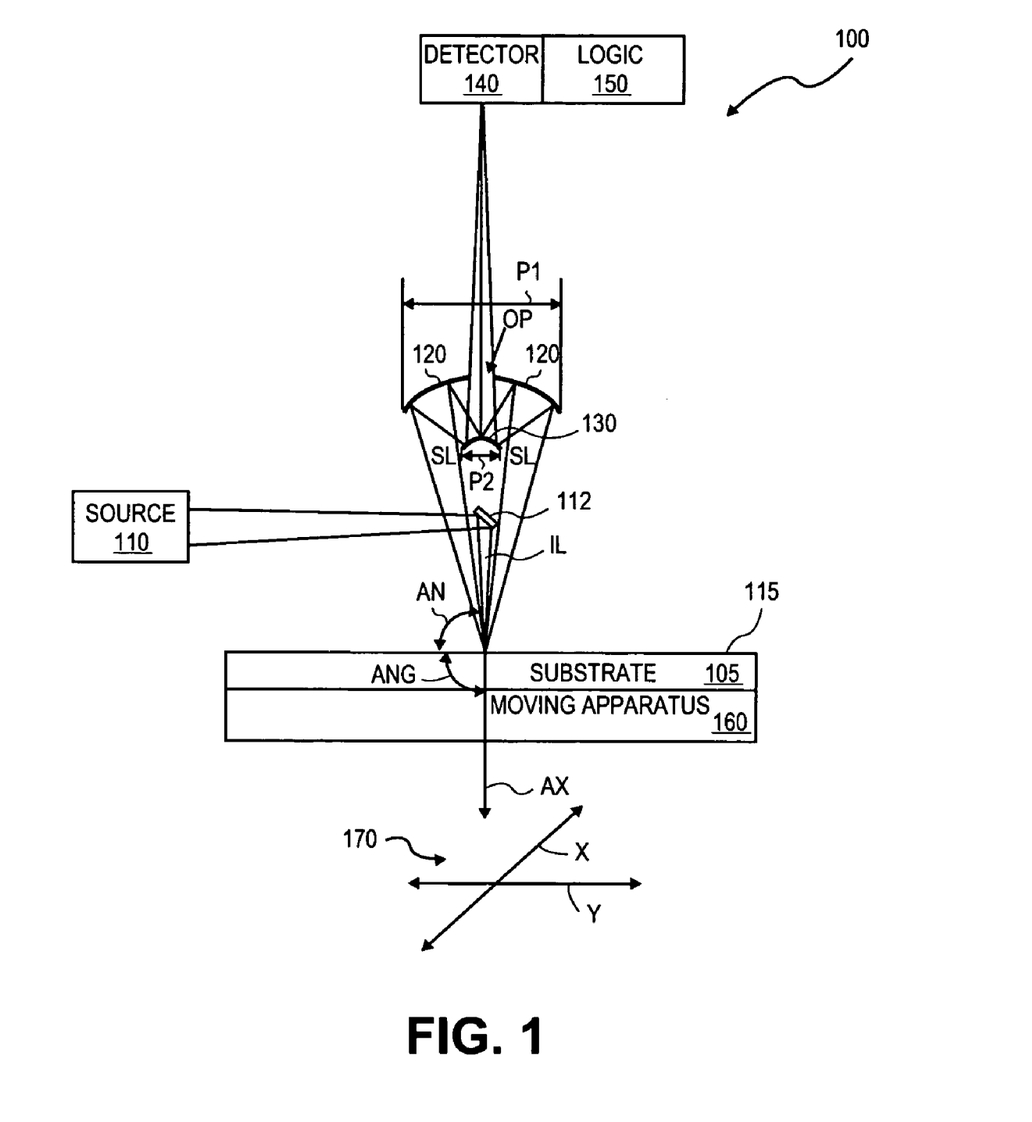
FIG. 1 is one embodiment of a system for inspecting a multi-layered mask blank.

FIG. 1 is one embodiment of a system for inspecting multi-layered mask blanks. FIG. 1 shows system 100 having source 110 to illuminate substrate 105. Source 110 may provide (e.g., reflect) incident light IL to substrate 105 using source mirror 112 (e.g., such as a spherical mirror or aspherical mirror). Light from source 110 may be focused by source mirror 112 onto surface 115 of substrate 105, below surface 115 of substrate 105, or above surface 115 of substrate 105.

In addition, source 110 may be an illumination apparatus, such as a source of light, ultraviolet (UV) light, extreme ultraviolet (EUV) light, or other light appropriate for patterning a light sensitive material on a substrate or wafer, or for inspecting an etch or patterning mask blank. Accordingly, source 110 may provide light having a wavelength in the range of 10 to 400 nanometers (e.g., UV light), such as by providing light having a wavelength of 20 nanometers, 50 nanometers, 100 nanometers, 150 nanometers, or 175 nanometers. Specifically, source 110 may produce light such that incident light IL is EUV light having a wavelength of between 10 nanometers and 200 nanometers, such as by having a wavelength of 11 nanometers, 12 nanometers, 13 nanometers, 13.5 nanometers, 14 nanometers, 15 nanometers, or 16 nanometers. In addition, light source 110 may include a filter, such as a filter to ensure that the wavelength or incident light IL is in a desired range, such as within the EUV range of 10 nm to 200 nm, as specified above.

Substrate 105 may be a substrate or wafer including multiple layers of a reflective material, a multi-layered patterning mask, a patterning mask, an etch mask, a lithographic mask, a photolithography mask, a photo mask, or a mask blank thereof. Thus, it is contemplated that source 110 and source mirror 112 are sufficient to illuminate bumps or irregularities in the height of surface 115 or layers below surface 115 of substrate 105. For instance, substrate 105 may be a plate or substrate having multiple layers of reflective material of molybdenum (Mo) and silicon (Si) formed thereon, and source 110 may provide incident light IL having an appropriate wavelength, intensity, and focus to illuminate or penetrate all of the layers of Mo and Si formed thereon.

Thus, substrate 105 may be a patterning or etch mask blank, such as a substrate or plate having multiple layers of molybdenum (Mo) or silicon (Si) formed thereon in an alternating layered order, where surface 115 is the surface of a top layer of molybdenum (Mo) or silicon (Si), prior to the mask blank having a buffer layer and absorber layer deposited on surface 115. Specifically, surface 115 may have a buffer layer formed thereon; an absorber layer formed on the buffer layer; a pattern patterned, written, or etched in the absorber layer; and then have a pattern written or etched into the buffer layer (e.g., to form a patterning mask). It is also to be appreciated that this process may include repair of the absorber layer (such as during patterning, writing, or etching). Thus, substrate 105 may be a mask blank of a mask to be formed for patterning or etching a silicon wafer, such as a wafer on which electronic semiconductor devices are being formed, using EUV patterning of a light sensitive material formed or layered on the wafer.

It is also contemplated that substrate 105 may have between 10 and 60 layers (e.g., such as by having between 10 and 60 layers of Mo and Si material). For example, substrate 105 may include 20, 25, 30, 35, 40, 45, or 50 layers of Mo and Si material where each layer is one layer of either Mo or Si material of an alternating Mo Si layer structure. In addition, each of the Mo or Si layers may be a reflective layer, such as a layer capable of partially reflecting EUV light. For example, incident light IL may penetrate all of the multi-layers of substrate 105 (e.g., such as by penetrating 35, 40, or 45 layers of Mo and Si without being completely absorbed and/or reflected by those layers).

Because the EUV light can have light intensity spread over a light frequency bandwidth (e.g., such as by having light intensity across a bandwidth of frequencies as large as about two percent of the selected or desired frequency of the light), it is useful to describe the frequency of EUV light, such as incident light IL, in terms of "centroid wavelength". A centroid wavelength may represent a wavelength at which is located the mean value across the bandwidth of the intensity of EUV light used or radiated.

According to embodiments, source 110 may generate incident light IL having an EUV light whose centroid wavelength is between 1.005 and 1.010 times the centroid wavelength of a light used to pattern or expose portions of a light sensitive material on a wafer during a photolithographic process where portions corresponding to a pattern formed on substrate 105 of reflective multi-layers (as compared to light absorbing material formed on the reflective multi-layers) are formed in the light sensitive material of the wafer. For example, incident light IL may have a centroid wavelength of 1.006, 1.007, 1.008, or 1.009 times a centroid wavelength of a patterning light used to expose portions of light sensitive material on a wafer being patterned with a patterning mask formed from the mask blank being inspected by incident light IL.

Moreover, it is considered that the light used to expose the light sensitive material on the wafer may be incident upon surface 115, substrate 105, and/or the light sensitive material of the wafer at an angle of between six degrees and eight degrees from perpendicular to surface 115 (e.g., such as by being at an angle of between 6 degrees and 8 degrees from axis AX of mirror 120, as shown in FIG. 1). For example, the patterning light used to expose the light sensitive material on the wafer may be incident at an angle of 6.5 degrees, 7 degrees, or 7.5 degrees from axis AX.

FIG. 1 also shows scattered light SL such as dark-field imaging light scattered, diffused, or reflected from substrate 105. Specifically, scattered light SL may include reflected light, scattered light, diffused light, caused by illumination of multiple Mo and Si layers of substrate 105 by incident light IL. However, according to embodiments, scattered light SL may exclude a portion of or all of specular reflection of incident light IL from substrate 105. Thus, according to embodiments, incident light IL may be completely reflected by layers of reflective material that are part of substrate 105 (e.g., such as layers of Mo or Si material formed on a substrate or plate as described herein). Specifically, incident light IL may be reflected, scattered, or diffused by the layer that forms surface 115 of substrate 105 as well as one or more layers of multi-layer material of substrate 105 below surface 115 (e.g., such as multiple layers of Mo and Si material on which a surface layer of Mo or Si is formed).

Furthermore, according to embodiments, scattered light SL may include a portion or all of incident light IL reflected, scattered, or diffused by substrate 105. Thus, when incident light IL encounters a bump or irregularity on or below surface 115, the magnitude or brightness of scattered light SL may increase while the magnitude or brightness of specular reflection decreases.

Mirror 120 may be used to gather all or a portion of scattered light SL. Mirror 120 may be a spherical mirror having perimeter P1 (e.g., such as a diameter) and opening OP. In addition, mirror 120 may be designed to reflect scattered light SL to mirror 130. Mirror 130 may also be a spherical mirror having perimeter P2 (e.g., such as a diameter) smaller than perimeter P1. Mirror 130 may be designed to reflect a portion or all of the scattered light received from mirror 120 to a detector. For example, mirror 130 may reflect that light through opening OP to detector 140.

According to embodiments, mirror 120 and mirror 130 may be mirrors having a spherical shape including less than 20% of a sphere by surface area. Specifically, mirror 120 may have a numerical aperture (NA) of 0.2 and have a concave spherical shape. Likewise, mirror 130 may have an NA of 0.1 and have a convex-shaped spherical reflective surface.

Furthermore, according to embodiments, opening OP may have a diameter less then or equal to perimeter P2 of mirror 130. More particularly, opening OP (e.g., such as a diameter of opening OP) may be larger than the trace or cross-sectional shape of a light ray which is reflected at the edges or perimeter P2 of mirror 130. Mirror 120, mirror 130, and opening OP may be part of a "Schwarzschild Optics" device.

Detector 140 may be a device for detecting light, such as UV or EUV light. For example, detector 140 may be a camera or electronic-type image sensing array (ISA), such as a charge-coupled device (CCD), or various other appropriate pixel imaging technology able to capture scattered light reflected to detector 140.

As shown in FIG. 1, source mirror 112 may be aligned or disposed along axis AX of mirror 120. Similarly, detector 140 may be oriented or disposed along axis AX. Moreover, axis AX may be oriented perpendicular to surface 115 of substrate 105. Also, it is considered that there may be angle AN between the outermost ray of the illumination of incident light IL or the half cone angle of the illumination of incident light IL and surface 115. In one case, angle AN may be between 85 and 90 degrees, such as by being 86 degrees, 87 degrees, 88 degrees, or 89 degrees.

FIG. 1 also shows moving apparatus 160 attached to substrate 105. Moving apparatus 160 may be an apparatus sufficient to move surface 115 in three dimensions with respect to axis AX. For example, FIG. 1 shows axes 170 having an "X" axis and a "Y" axis forming a two dimensional plane that may be parallel to surface 115. Thus, moving apparatus 160 may move surface 115 along the "X" "Y" plane of axes 170, in two dimensions with respect to axis AX. Specifically, moving apparatus 160 may move substrate 105 with respect to incident light IL so that incident light IL is incident upon all or a portion of surface 115. Moreover, moving apparatus 160 may move substrate 105 so that source mirror 112, mirror 120, and detector 140 are oriented or disposed along axis AX at an angle with respect to surface 115 as described above (e.g., such as where axis AX is oriented perpendicular to surface 115).

In addition, to focus the Schwarzschild Optics with respect to substrate 105 (e.g., such that the focus of mirror 112 and/or mirror 120 are at surface 115, or at a desired depth below surface 115), moving apparatus 160 may move substrate 105 along axis AX (e.g., the third dimension with respect to axis AX) so that source mirror 112, mirror 120, and detector 140 are oriented or disposed along axis AX (e.g., such as by those devices being located along axis AX at an appropriate distance from surface 115 to focus one or more of the mirrors as desired).

According to embodiments, moving apparatus 160 can be a servo stage that can have a mask blank set on it and that can be controlled by a computer. For instance, moving apparatus 160 may have a platform or surface on which substrate 105 is placed or attached (e.g., such as removably attached by physical restraints or adhesive). Moving apparatus may further include one or more servos, that are controlled by a computer (e.g., such as according to a machine accessible medium having instructions for execution by a machine, or a software routine), to move the substrate in three dimensions, as described above.

In addition, system 100 or components thereof may exist in a vacuum setting, for example, light provided by source 110, incident light IL, substrate 105, scattered light SL, mirror 120, mirror 130, and light reflected by mirror 130 to detector 140 may exist in a vacuum sufficient to allow for propagation of EUV light sufficient for systems and processes described herein. Thus, it can be appreciated that system 100, substrate 105, multiple layers of reflective material on substrate 105 (e.g., such as alternating layers of Mo and Si formed on and below surface 115) and a patterning mask formed from substrate 105 (e.g., such as where substrate 105 is a mask blank) may be designed, configured, and use optics and pressure appropriate for transmission of EUV light). For instance, those devices may be designed without lenses or glass through which the EUV light is to pass (e.g., since EUV light does not pass through glass) and may be designed to only have the EUV light travel in a vacuum (e.g., since EUV light does not travel far in an atmosphere such as air).

Figure 2:
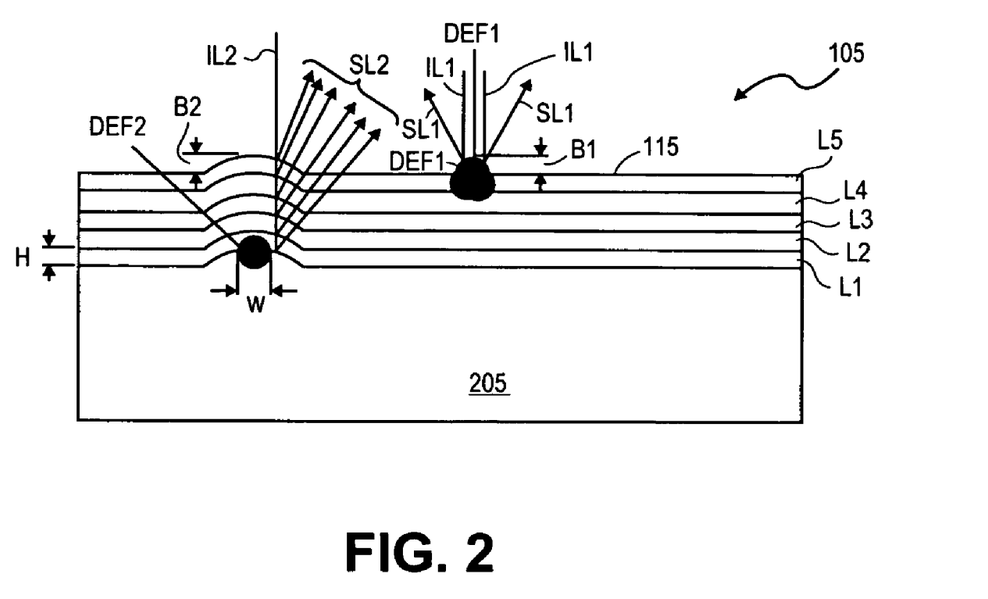
FIG. 2 is a cross-sectional view of a multi-layered mask blank.

As noted above, incident light IL may gradually penetrate, be reflected by and/or be absorbed by the multiple layers of substrate 105. For example, FIG. 2 is a cross-sectional view of a multi-layered mask blank. FIG. 2 shows substrate 105 having substrate 205 and first layer L1, second layer L2, third layer L3, fourth layer L4, and fifth layer L5 formed on top of substrate 205. As mentioned above, it is contemplated that substrate 105 may include between 10 and 60 layers, thus layers L1 through L5 may be representative of a portion of the total layers of a multi-layer mask blank. As shown in FIG. 2, surface 115 is the surface of fifth layer L5. Thus, incident light IL, incident upon substrate 105, may be scattered or diffused by defect DEF1 which has form bump B1 above surface 115, such as is shown by scattered light SL1 in FIG. 2. Similarly, where incident light IL is EUV light, defect DEF2 may scatter or diffuse EUV light EUV by causing deformations or bumps in layers L1 through L5, such as is shown by SL2 in FIG. 2.

Thus, system 100 of FIG. 1 may be able to detect abnormalities, bumps, or defects within the layers of substrate 105, by using dark-field imaging optics to gather the scattered, reflected, or diffused light resulting from the abnormalities, bumps, or defects in the multiple layers resulting from the defect. It is contemplated that system 100 may be able to detect defects having a height between 2 nanometers (nm) and 8 nanometers in height (e.g., see height H of defect DEF2 of FIG. 2), and having a width of between 35 nm and 94 nm (such as width W of defect DEF2 as shown in FIG. 2). For instance, a defect having a height and width as described above may cause abnormalities, bumps, or defects in the planarity of the multiple layers of the mask blank, thus causing diffusion or scattering of EUV light incident upon those layers. The scattered or diffused light may be gathered, measured or detected by system 100 such as by mirrors 120 and 130, which reflect scattered light SL to detector 140, which measures the intensity or amount of the scattered light. It can be appreciated that such defects may be a bump or abnormality at or below surface 115 (e.g., such as a defect or bump of unwanted material or space within the layers of substrate 105).

For instance, system 100 of FIG. 1 may detect a defect having a width of between 60 to 70 nm, and a height of 2 nm or greater as a critical defect. Thus, apparatus 100 may be able to detect a defect at an approximate lower-layer level, such as at layers 35–40 below surface 115 of 40 layers, having a 60 nm width and a height of 2 nm or greater, that forms a bump of between 0.4 and 2.3 nm in height at surface 115. Likewise, apparatus 100 may detect a defect at an approximate mid-layer lever, such as at layer 15 below surface 115 of 40 layers, that creates a bump at surface 115 of 2.3 m in height.

Specifically, as shown in FIG. 2, system 100 may be able to detect, identify, and locate defect DEF2 having height H of 3 nm, 4 nm, 5 nm, 6 nm, or 7 nm and producing bump height B2 of zero or more nanometers at surface 115 by measuring scattered light SL2 reflected by layers L1 through L5 of substrate 105 when those layers are illuminated by incident light IL2. Similarly, system 100 may detect, identify, and locate defect DEF1 having bump height B1 of 2 mm, 2.5 nm, 3 nm, or 4 mm at surface 115 by measuring scattered light SL1 resulting from illuminating substrate 105 and defect DEF1 with incident light IL1.

FIG. 1 also shows logic 150 connected to detector 140. For example, logic 150 includes logic circuitry, gates, computer logic hardware, memories, comparators, and/or registers coupled to detector 140 to determine whether reflective, scattered, or diffused light received and measured from substrate 105 satisfies a criteria. Thus, logic 150 may include logic to detect, identify, and locate defects in substrate 105 (e.g., such as defects within the multiple layers of a multi-layer mask blank as described above with respect to FIG. 2). Specifically, "detecting" a defect as used herein may include measuring reflected light intensity values and normalizing those values for a number of pixels, as described herein. Also, "identifying" a defect as used herein may include determining whether the measured and normalized value of reflective light from the pixels satisfies criteria to indicate that a defect exists, such as described herein. Next, "locating" a defect as used herein may include determining a location of a defect, such as a location at one or more pixels where the defect exists, as described herein.

In one instance, logic 150 may determine whether a pixel threshold value is satisfied by a pixel reflective light intensity value received by detector 140 for a first pixel of substrate 105, where substrate 105 is a multi-layered patterning mask blank. It is considered that the pixel reflective light intensity value received by detector 140 may be normalized as described below with respect to FIG. 3, prior to logic 150 determining whether the threshold value is satisfied. For example, logic 150 may determine whether the normalized scattered light intensity value at center pixel CP is greater than a pixel threshold value, thus identifying center pixel CP as a candidate for a location with a defect.

In addition, logic 150 may determine whether a pixel block threshold value is satisfied by a sum of pixel reflective light intensity values received from detector 140 for a number of pixels of a pixel block of a multi-layer mask, where the pixel block includes the pixel compared to the first threshold value. It is considered that the pixel reflective light intensity values received by detector 140 for the number of pixels of the pixel block may each be normalized as described below with respect to FIG. 3, prior to logic 150 determining whether the second threshold value is satisfied. For example, logic 150 may determine whether the scattered light reflected by multiple pixels around and including center pixel CP, when normalized and summed together, satisfy a pixel block threshold, to determine whether the pixel block scatters a critical amount of light, such as an amount of reflected light that would correspond to a "critical defect" (e.g., such as a selected amount of light appropriate for apparatus 100, substrate 105, and the multi-layers of substrate 105 to satisfy a defect tolerance or threshold for a selected critical defect size).

Hence, system 100 may detect abnormalities, bumps, or imperfections in the planarity or flatness of layers L1 through L5 of substrate 105 as shown in FIG. 2 at a microscopic level (e.g., such as for pixels having a size of less than 1.0 $\mu$m) to identify and locate defects, such as errant materials or bumps of materials in or on the surface, or layers (e.g., such as layers L1 through L5) of substrate 105 by having logic 150 consider bright spots in the dark-field image of scattered or diffused light reflected from the surface and layers of substrate 120 when substrate 120 is illuminated with incident light IL. It is also contemplated that logic 150 may be implemented by hardware and/or software, such as digital code or instructions, or a machine-accessible medium containing instructions that cause a machine to perform the functionality described herein with respect to logic 150.

Surface 115 of substrate 105 may include or define a grid of pixels (e.g., such as grid 300 of FIG. 3 and grid 400 of FIG. 4 as described below), that system 100 inspects, as described herein. Thus, reflected scattered light intensities may be measured for each pixel of the grid, then a normalized scattered light value may be calculated for each pixel of the grid, then logic 150 may determine whether criteria are met for various groups of the pixels of the grid to identify defects within the grid.

Figure 3:
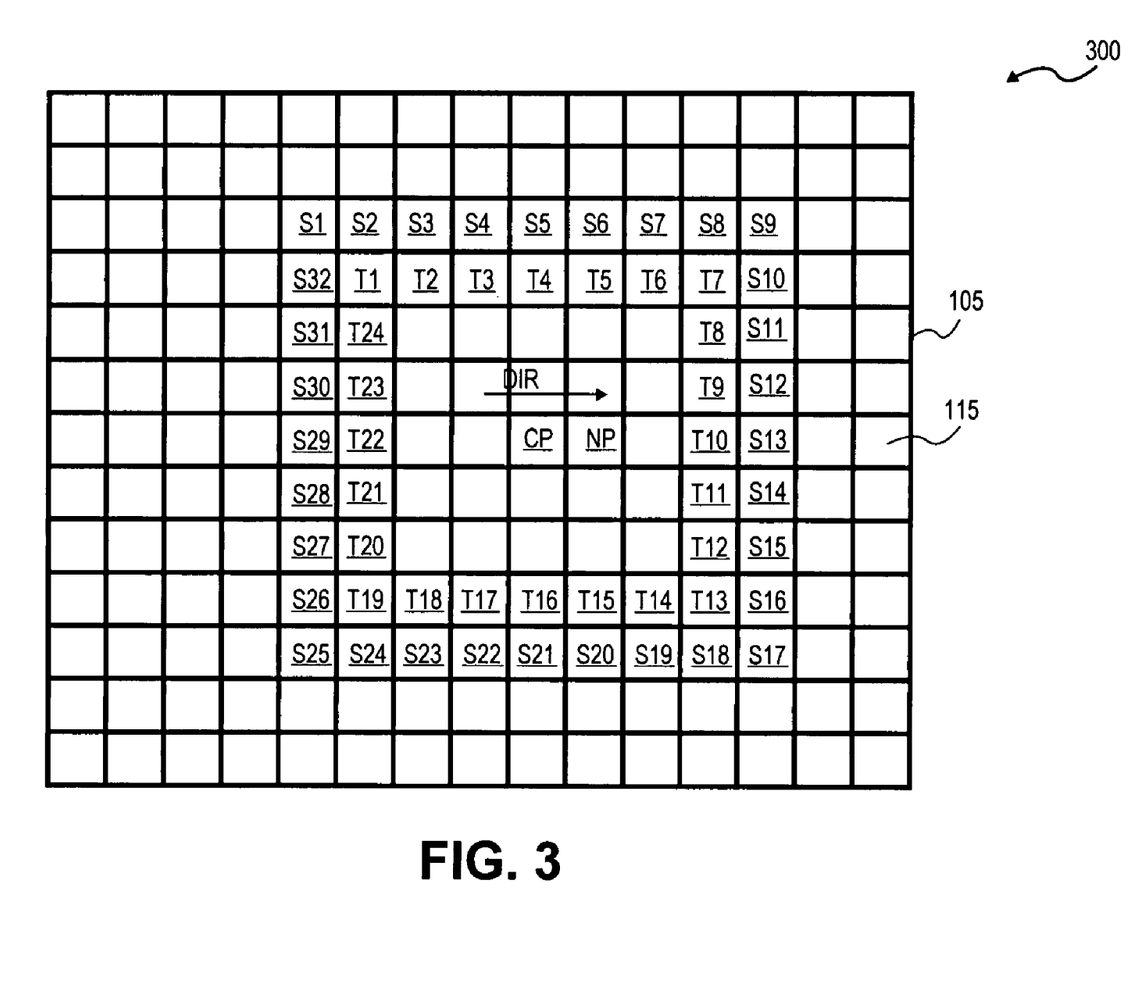
FIG. 3 is a top perspective view of a multi-layered mask blank.

For example, FIG. 3 is a top perspective view of a multi-layer mask blank. FIG. 3 shows an array of pixels, such as grid of pixels 300, center pixel CP, and next pixel NP in direction DIR from center pixel CP. Surrounding center pixel CP is inner perimeter of pixels T1, T2, T3, T4, T5, T6, T7, T8, T9, T10, T11, T12, T13, T14, T15, T16, T17, T18, T19, T20, T21, T22, T23, and T24. Surrounding inner perimeter of pixels T1–T24 is outer perimeter of pixels S1, S2, S3, S4, S5, S6, S7, S8, S9, S10, S11, S12, S13, S14, S15, S16, S17, S18, S19, S20, S21, S22, S23, S24, S25, S26, S27, S28, S29, S30, S31, and S32.

According to embodiments, grid of pixels 300 may be pixels on or associated with substrate 105. For example, grid of pixels 300 may be pixels identified or mapped out with respect to surface 115. Specifically, the pixels of grid of pixels 300 (e.g., such as center pixel CP, next pixel NP, each of inner perimeter of pixels T1–T24, and each of outer perimeter of pixels S1–S32) may be pixels having a pixel size as described above with respect to FIGS. 1 and 2, and may include layers of a multi-layer patterning mask blank as described herein. Thus, pixels of grid of pixels 300 may correspond to pixels from which scattered, reflected, or diffused light intensity values or measurements are made as described herein. For example, system 100 may illuminate pixels of grid of pixels 300 with incident light IL and measure scattered light SL reflected by each pixel, as a result.

More particularly, according to embodiments, system 100, mirrors 120 and 130, source 110 and/or detector 140 may include Schwarzschild Optics or dark-field optics that have a magnification of 20×, use an incident light wavelength of 13.5 nm, and/or use a detector CCD having a pixel size of 13.5 $\mu$m to measure scattered light from pixels of grid of pixels 300. For example, system 100 may detect scattered or diffused light, such as scattered light SL, for a pixel having a width and length of between 0.3 $\mu$m and 0.8 $\mu$m. Specifically, detector 140 may have a pixel size of 13.5 $\mu$m (e.g., pixel size of detection at detector 140) and the "Schwarzschild Optics" or dark-field imaging optics of system 100 may have a magnification of 20×, thus resulting in system 100 being able to sufficiently illuminate a pixel with incident light IL and measure the resulting scattered light SL for a resolution or pixel size as small as 13.5 $\mu$m divided by 20, or a pixel size equal to 0.675 $\mu$m (e.g., a pixel size of a pixel, such as center pixel CP of FIG. 3). System 100 may also detect light from pixels having a size of 0.35 $\mu$m, 0.4 $\mu$m, 0.45 $\mu$m, 0.5 $\mu$m, 0.55 $\mu$m, 0.6 $\mu$m, 0.65 $\mu$m, 0.7 $\mu$m, 0.8 $\mu$m.

Referring to FIG. 3, a normalized light intensity value may be determined for center pixel CP by measuring a reflective light intensity value (e.g., such as a scattered or diffused reflection light value measured by dark-field imaging optics and/or system 100) for center pixel CP (e.g., such as a reflective light intensity value that includes reflection of incident light IL from the surface as well as layers below the surface of substrate 105 at pixel CP) and for at least one surrounding ring of other pixels. In one instance, reflective light intensity values for inner perimeter of pixels T1 through T24 are also measured. Likewise, reflective light intensity values for outer perimeter of pixels S1 through S32 are measured. Then, the normalized light intensity value for center pixel CP is calculated as the reflective light intensity value measured for center pixel CP divided by the average of the light intensity values for both the inner perimeter of pixels T1 through T24 and the outer perimeter of pixels S1 through S32. In other words, (normalized light intensity value for center pixel CP)=(light intensity value for center pixel CP)/((some of light intensity values for pixels T1 through T24+some of light intensity values for pixels S1 through S32)/56).

It is also contemplated that the denominator of the calculation for determining the normalized light intensity value above may instead be the average of: (1) only perimeter of pixels T1 through T24, (2) only outer perimeter of pixels S1 through S32, or (3) one or more shapes or perimeters of pixels other than those shown in FIG. 3. For example, the denominator of the equation above for determining normalized light intensity values may be one or more perimeters in the shape of a trapezoid, a rectangle, a square, and a ring of pixels around center pixel CP. Furthermore, it may be appreciated that the calculations described above for determining a normalized light intensity value may be performed on each pixel in grid of pixels 300. For example, the processes and calculations described above may be repeated for next pixel NP, by moving perimeter of pixels T1 through T24 and outer perimeter of pixels S1 through S32 one pixel in the direction of direction DIR, and recalculating as described above to determine the normalized light intensity value for next pixel NP.

Figure 4:
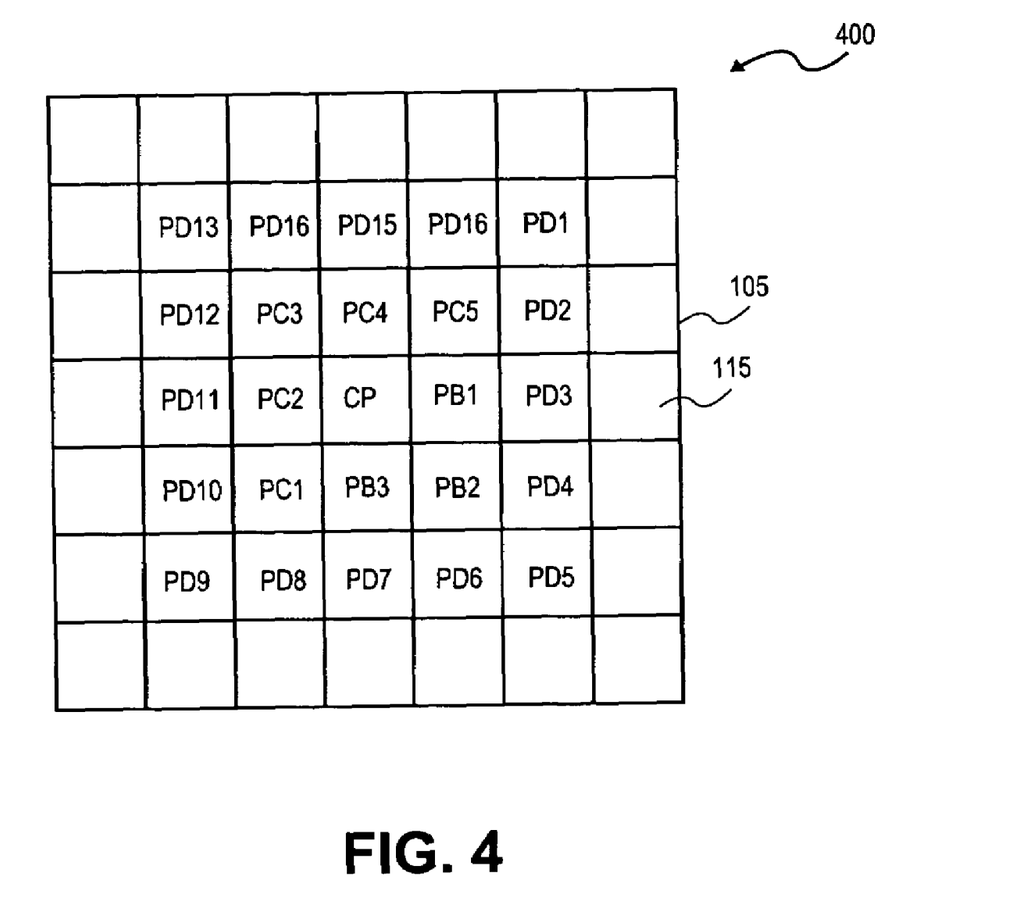
FIG. 4 is a top perspective view of a multi-layered mask blank.

Furthermore, according to embodiments, the light intensity values of EUV light reflected at pixels of grid of pixels 300 may be considered to determine criteria, such as to determine whether a defect exists in a multi-layered mask blank. For example, FIG. 4 is a top perspective view of a multi-layered mask blank. FIG. 4 is a grid of pixels having a center pixel and blocks of pixels including the center pixel. FIG. 4 shows grid of pixels 400 having center pixel CP; a first block of four pixels including center pixel CP; a second block of nine pixels including the first block of pixels; and a third block of twenty-five pixels including the second block of pixels. For example, reflected light intensity values for the pixels of grid of pixels 400 may be considered, measured, or determined according to reflected EUV light intensity values of scattered light, diffused light, or reflected light resulting from incident light IL, as described above with respect to system 100. Moreover, grid of pixels 400 may be a grid of pixels as described above with respect to grid of pixels 300. Consequently, the pixels of grid of pixels 400 may be pixels on substrate 105 or surface 115.

According to embodiments, whether a defect exists may be determined by considering a reflective EUV light intensity value for center pixel CP and by considering a light intensity value for a block of pixels including center pixel CP and (e.g., such as a block of more than one pixel). It is contemplated that considering the reflected EUV intensity light value of a pixel includes considering the normalized light intensity value as described above with respect to FIG. 3. Thus, identifying a defect at center pixel CP of grid of pixels 400 may be performed by considering whether the normalized light intensity value of center pixel CP qualifies center pixel CP as a candidate of a location with a defect, and by considering whether the normalized light intensity value of a block of pixels (e.g., such as a block having at least two pixels and including center pixel CP), verifies the criticality of the intensity of the normalized light values of the block of pixels as scattering or diffusing enough light to indicate a critical defect.

According to embodiments, the block of pixels to verify the criticality of the intensity may be a block of two pixels, a block of three pixels, a block of four pixels, a block of nine pixels, a block of ten pixels, a block of twenty-five pixels, or a block of thirty-six pixels. Specifically, as shown in FIG. 4, for instance, the block of pixels may include center pixel CP and pixel PB1. Also, the pixel block may include center pixel CP, pixel PB1, pixel PB2, and pixel PB3. Moreover, the pixel block may include pixels PB1 through PB3, pixel PC1, pixel PC2, pixel PC3, pixel PC4, and pixel PC5 (e.g., such as with or without center pixel CP). Additionally, the pixel block may include pixel PD1, pixel PD2, pixel PD3, pixel PD4, pixel PD5, pixel PD6, pixel PD7, pixel PD8, pixel PD9, pixel PD10, pixel PD11, pixel PD12, pixel PD13, pixel PD14, pixel PD15, and pixel PD16; with or without pixels PB1 through PB3, pixels PC1 through PC5, and/or center pixel CP.

Thus, in one embodiment, it may be determined whether the normalized scattered or diffused light reflection at center pixel CP satisfies a first threshold and whether the normalized scattered or diffused light reflection for the pixel block satisfies a second threshold in order to identify if a defect is present at center pixel CP, or at the location of the pixel block. It is to be appreciated that determining whether a threshold value is satisfied may include determining whether a light intensity value is greater than a threshold value, or greater than or equal to a threshold value.

Figure 5:
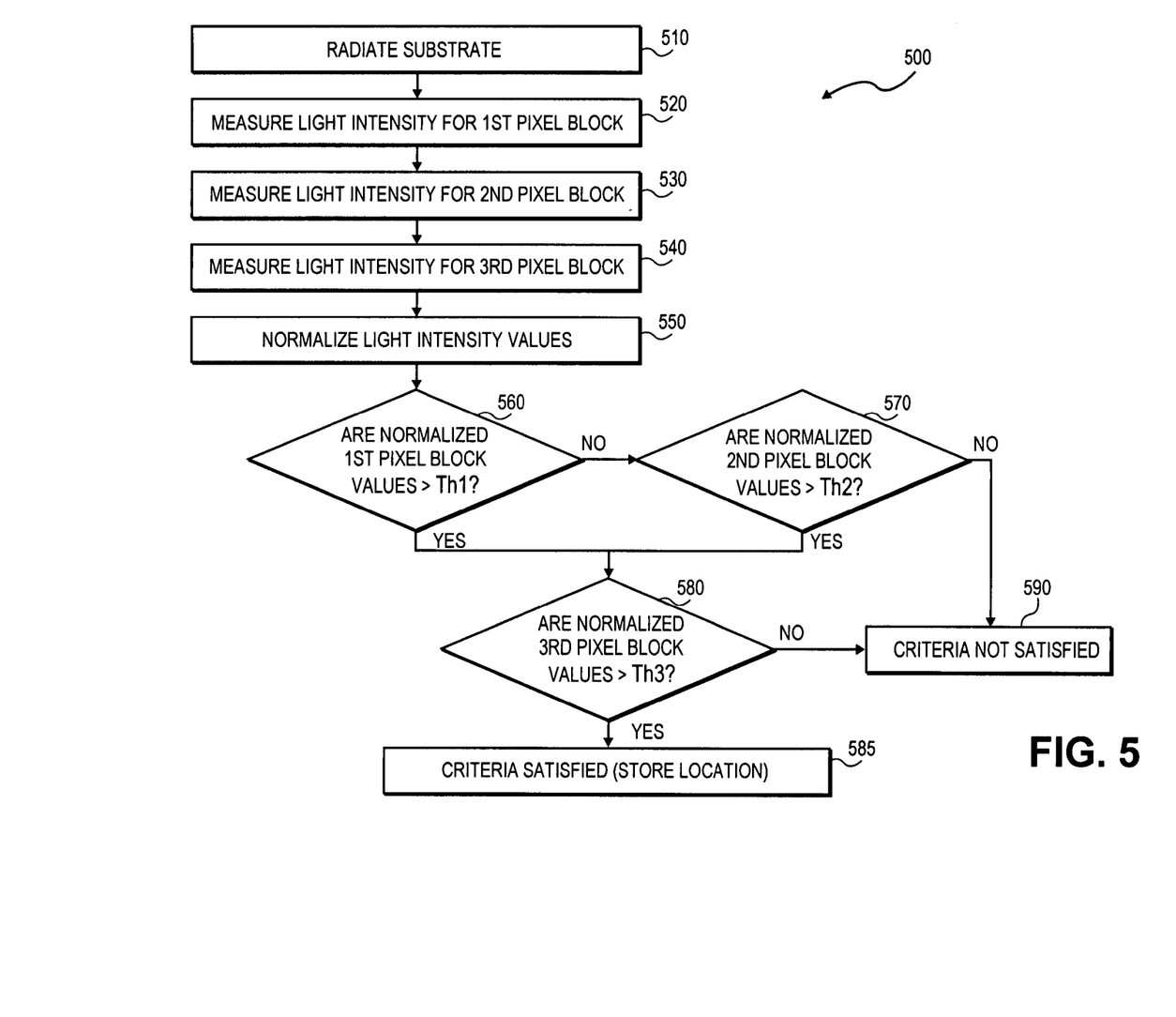
FIG. 5 is a flow diagram of a process for locating defects in a multi-layered mask blank.

FIG. 5 is a flow diagram of a process for locating defects in a multi-layered mask blank. At block 510 a substrate is radiated with EUV light. For example, block 510 may correspond to descriptions above with respect to radiating or illuminating substrate 105 with incident light IL. In addition, block 510 may correspond to descriptions of radiating or illuminating grid of pixels 200 and/or grid of pixels 300 of substrate 105. Moreover, block 510 may correspond to illuminating the surface and layers below the surface of a multi-layered patterning or etching mask blank as described herein.

At block 520, the light intensity for a first pixel block is measured. Block 520 may correspond to measuring the scattered or diffused light for center pixel CP, or a pixel block as described above with respect to FIG. 4. For example, block 520 may include measuring reflected light, detecting reflected light, dark-field image detection, scattered light reflection measurement, or diffuse light reflection measurement of incident IL as reflected by the first pixel block as described above will respect to FIG. 4.

At block 530, the light intensity value for a second pixel block is measured. For example, the second pixel block may correspond to a pixel block as described above with respect to FIG. 4 and including the first pixel block, such as where the second pixel block is larger than the first pixel block. Block 530 may correspond to measuring light intensity values as described above with respect to block 520, but for a second pixel block as described above with respect to FIG. 4.

At block 540, light intensity values for a third pixel block are measured. Block 540 may correspond to measuring light intensity values for a pixel block as described above with respect to FIG. 4, where the third pixel block includes and is larger than the second pixel block. Measuring light intensity values at block 540 may correspond to measuring light intensity values as described above with respect to block 520, but for a third pixel block as described above with respect to FIG. 4.

At block 550, the light intensity values measured at block 520, 530, and 540 are normalized. For example, the light intensity measured for each pixel of the first, second, and third pixel block may be divided by an average of a number of UV light reflection measurements for a number of pixels surrounding each of the pixels of the first, second, and third pixel blocks. In addition, the normalizing of block 550 may correspond to descriptions above for normalizing light intensity values as described with respect to FIG. 3.

At decision block 560, it is determined whether the normalized first pixel block value or values satisfy or are greater than first threshold Th1. For example, at block 560, it may be determined whether the normalized reflected light intensity value of a first pixel block as described for FIG. 4 (e.g., such as of center pixel CP) is greater than first threshold Th1. If at block 560 the normalized first pixel block value or values are not greater than first threshold Th1, then the process continues to block 570.

At block 570, it is determined whether the normalized pixel block values of the second pixel block are greater than second threshold Th2. For example, at block 570, it may be determined whether the normalized reflected light intensity values for a second pixel block as described for FIG. 4 (e.g., such as for center pixel CP plus pixels PB1 through PB3) are greater than second threshold Th2. If at block 570 the pixel block values are not greater than the second threshold, the process continues to block 590.

If at block 560, the pixel block values or value is greater than the first threshold, or if at block 570 the sum of the second pixel block values is greater than the second threshold, then the process continues to decision block 580. At decision block 580, it is determined whether the normalized third pixel block values are greater than third threshold Th3. For example, at block 580, it may be determined whether the sum of the reflected light intensity values for a third pixel block as described for FIG. 4 (e.g., such as for center pixel CP, plus pixels PB1 through PB3, plus pixels PC1 through PC5) are greater than third threshold Th3. It is also considered that at block 580 it may be determined whether the reflected light intensity values for pixels PD1 through PD16, pixels PB1 through PB3, pixels PC1 through PC5, and center pixel CP are greater than a third threshold.

If at block 580 the sum of the normalized third pixel block values is not greater than third threshold Th3, then the process continues to block 590.

At block 590, it is determined that the criteria is not satisfied. For example, at block 590, it may be determined that a defect does not exist at center pixel CP, at the second pixel block, or at the third pixel block. Thus, according to FIG. 5, the criteria may not be satisfied when either the second or third pixel block fails to meet the second or third threshold, respectively. In other words, decision blocks 560 and 570 may be used to identify candidates of locations with defects, while block 580 may be used to verify whether there is a criticality of scattered light intensity by checking the summed intensity within nine to twenty-five pixels around center pixel CP because EUV light scattered by a defect may be imaged in a wide area due to the defect causing a large field with a curved focal plane within the multi-layers of the mask blank.

If at decision block 580 the sum of the normalized third pixel block values is greater than the third threshold, then the process continues to block 585. At block 585, it is determined that the criteria is satisfied. For example, at block 585, it may be determined that a defect exists at center pixel CP, at the first pixel block, at the second pixel block, or at the third pixel block. Furthermore, at block 585, the location of the defect, as described above, may be stored (e.g., such as storing in a memory or register the location or identification of the pixel or pixel block corresponding to the defect).

After block 585 or block 590, it is contemplated that process 500 may move the location for center pixel CP to a next pixel of a grid of pixels and inspect the grid of pixels to determine whether a defect exists at or about the location of the next pixel. For example, after block 585 or block 590, process 500 may continue and inspect next pixel NP as described above with respect to FIG. 3 (e.g., such as by moving all pixel locations considered one pixel in direction DIR) and then considering new first, second, and third pixel blocks, such as is described above with respect to FIGS. 4 and 5.

In addition, it is contemplated that block 560 may correspond to the following equation:

$$A_{m,n} > Th1 \qquad\qquad A$$

wherein $A_{m,n}$ is the normalized reflective light intensity value detected at a pixel located at position (m,n) of a grid of pixels (e.g., such as where m corresponds to a position in the X direction of axes 170, and n corresponds to a position with respect to the Y direction of axes 170, as shown in FIG. 1); and Th1 represents the first threshold.

Correspondingly, block 570 may correspond to the following equation:

$$\sum_{i,j=0}^{1} A_{m+i,n+j} > Th2 \qquad\qquad B$$

wherein $A_{m+i,n+j}$ represent the normalized reflected light intensity value at pixels located adjacent to and including pixel $A_{m,n}$, as described above for equation A; and Th2 represents a second threshold. Thus, equation B may represent the sum of normalized reflected light intensity values for a pixel block.

Next, block 580 may correspond to the following equation:

$$\sum_{i,j=-1}^{1} A_{m+i,n+j} > Th \qquad\qquad C$$

wherein $A_{m+i,n+j}$ equals the normalized reflected light intensity values for pixels adjacent to or forming a perimeter around pixel $A_{m,n}$, such as is described above with respect to equation A; and Th3 is the third threshold. Thus, equation C may represent the sum of normalized pixel reflective light intensity values for a block of pixels larger than the block of pixels summed in equation B, including the pixel block summed in equation B, and/or including pixel $A_{m,n}$.

In the foregoing specification, specific embodiments are described. However, various modifications and changes may be made thereto without departing from the broader spirit and scope of embodiments as set forth in the claims. The specification and drawings are, accordingly, to be regarded in an illustrative rather than a restrictive sense.

What is claimed is:

1. A method comprising:
   detecting a first light intensity value for a first pixel of a substrate;
   detecting a plurality of second light intensity values for a plurality of different second pixels of the substrate, the second pixels comprising an inner perimeter of pixels and an outer perimeter of pixels, wherein the outer perimeter of pixels has an outer perimeter equal to or larger than an outer perimeter of the inner perimeter of pixels, and wherein the first pixel is within the inner perimeter of pixels; and
   dividing the first light intensity value by an average of the second light intensity values.

2. The method of claim 1, wherein one of the inner perimeter and the outer perimeter form a shape of one of a trapezoid, a rectangle, a square, and a ring.

3. The method of claim 1, wherein the first and second light intensity values are one of scattered extreme ultraviolet (EUV) light reflection measurements and EUV dark-field image detections from a multi-layered mask blank.

4. The method of claim 1, further comprising repeating for a plurality of first pixels of the substrate:
   (a) detecting a first light intensity value;
   (b) detecting a plurality of second light intensity values; and
   (c) dividing a first light intensity value for respective ones of the plurality of first pixels by an average of the second light intensity values for respective pluralities of a corresponding plurality of second pixels.

5. A method comprising:
   radiating a multi-layered mask blank with an extreme ultraviolet (EUV) light;
   considering at least one first reflective EUV light intensity value determined for a first pixel block of the multi-layered mask blank; and
   considering a plurality of second reflective EUV light intensity values determined for a second pixel block of the multi-layered mask blank, the second pixel block including the first pixel block and having more pixels than the first pixel block.

6. The method of claim 5, wherein a criteria is satisfied if one of:
   the first EUV reflective light intensity value satisfies a first threshold value; and
   the plurality of second EUV reflective light intensity values satisfy a second threshold value.

7. The method of claim 6, wherein satisfaction of the criteria indicates a defect in the multi-layered mask blank at the first pixel block.

8. The method of claim 5, further comprising:
   considering a plurality of third reflective EUV light intensity values for a third pixel block of the multi-layered mask blank, the third pixel block including the second pixel block and having more pixels than the second pixel block.

9. The method of claim 8, wherein the criteria is satisfied if:
   one of (a) the at least one first reflective EUV light intensity value satisfies a first threshold value, and (b) the plurality of second reflective EUV light intensity values satisfy a second threshold value; and (c) the plurality of third reflective EUV light intensity values satisfy a third threshold value.

10. The method of claim 9, wherein satisfaction of the criteria indicates a defect in the multi-layered mask blank at one of the first pixel block and the second pixel block.

11. The method of claim 8, further comprising:
   measuring the first, second, and third reflective EUV light intensity values, wherein measuring includes one of a scattered light reflection measurement and a dark-field image detection; and
   normalizing the first, second, and third reflective EUV light intensity values by dividing each of the first, second, and third reflective EUV light intensity values by an average of a plurality of reflective EUV light values for a plurality of pixels surrounding each of the reflective EUV light values.

12. The method of claim 8, wherein the first size is one pixel block, the second size is at least two pixels, and the third size is at least 9 pixels.

13. The method of claim 8, wherein the first pixel block is one pixel, the second pixel block is a 2×2 pixel block, and the third pixel block is a 5×5 pixel block.

14. The method of claim 6, further comprising repeating determining whether a criteria is satisfied, for a plurality of first pixel blocks of the multi-layered mask blank.

* * * * *

UNITED STATES PATENT AND TRADEMARK OFFICE
CERTIFICATE OF CORRECTION

PATENT NO. : 7,005,649 B1  Page 1 of 1
APPLICATION NO. : 10/971786
DATED : February 28, 2006
INVENTOR(S) : Tezuka et al.

It is certified that error appears in the above-identified patent and that said Letters Patent is hereby corrected as shown below:

In column 6, at line 35, delete "m" and insert --nm--.
In column 6, at line 44, delete first occurrence of "mm" and insert --nm--.
In column 6, at line 44, delete second occurrence of "mm" and insert --nm--.
In column 10, at line 30, delete "will" and insert --with--.

Signed and Sealed this

Sixth Day of November, 2007

JON W. DUDAS
*Director of the United States Patent and Trademark Office*